(12) United States Patent
Murphy et al.

(10) Patent No.: US 6,984,636 B2
(45) Date of Patent: Jan. 10, 2006

(54) MITOCHONDRIALLY TARGETED ANTIOXIDANTS

(75) Inventors: Michael P. Murphy, Cambridge (GB); Robin A. J. Smith, Dunedin (NZ)

(73) Assignees: Medical Research Council (GB); University of Otago (NZ)

(*) Notice: Subject to any disclaimer, the term of this patent is extended or adjusted under 35 U.S.C. 154(b) by 241 days.

(21) Appl. No.: 10/217,022

(22) Filed: Aug. 12, 2002

(65) Prior Publication Data

US 2004/0029851 A1 Feb. 12, 2004

(51) Int. Cl.
*A61K 31/555* (2006.01)
*A61K 31/70* (2006.01)
*C07D 487/22* (2006.01)

(52) U.S. Cl. .................... 514/185; 514/184; 514/23; 514/53; 536/123.13; 546/2; 540/145

(58) Field of Classification Search ............... 514/185, 514/184, 23, 53; 536/123.13; 546/2; 540/145
See application file for complete search history.

(56) References Cited

U.S. PATENT DOCUMENTS

| 5,897,879 A | * | 4/1999 | Friedman et al. ........... 424/486 |
| 6,180,620 B1 | * | 1/2001 | Salvemini ................... 514/184 |
| 6,214,817 B1 | * | 4/2001 | Riley et al. ................. 514/186 |
| 6,331,532 B1 | | 12/2001 | Murphy et al. |

FOREIGN PATENT DOCUMENTS

| WO | WO 99/26582 | 6/1999 |
| WO | WO 99/26954 | 6/1999 |
| WO | WO 03/010154 | 2/2003 |

OTHER PUBLICATIONS

Kelso et al. (Journal of Inorganic Biochemistry, 86, 290 (2001).*
Andersson, C–M., et al., *Free Radical Biol. & Med.*, 16, 17–28 (1994).
Berge, et al., "Pharmaceutically Acceptable Salts," *J. Pharm. Sci.*, 66, 1–19 (1977).
Bobbit, J.M., *J. Org. Chem.*, 63, 9367–9374 (1998).
Boveris, A., *Methods Enzymol.*, 105, 429–435 (1984).
Burns and Murphy, *Arch Biochem Biophys*, 339, 33–39 (1997).
Burns, et al., *Arch Biochem Biophys*, 322, 60–68 (1995).
Burns, et al., *Arch Biochem Biophys*, 322, 60–68 (1995).
Chappell, J.B. and Hansford, R.G., In: *Subcellular components: preparation and fractionation* (Ed. Birnie GD), pp. 43–56, Butterworths, London, 1972.
Chaudiere, J, et al., "Design of New Selenium–Containing Mimics of Glutathione Peroxidase", 165–184, in *Oxidative Processes and Antioxidants*, edited by R. Paoletti, et al., Raven Press Ltd., New York (1994).
Chen, *Ann. Rev. Cell Biol.*, 4, 155–181 (1988).

Davey, G.P., et al., *Biochemical Journal*, 288, 439–443 (1992).
Engman, L., et al., *Chemico–Biological Interactions*, 93, 129–137 (1994).
Galet, V., et al., *J. Med. Chem.*, 37, 2903–2911 (1994).
Handbook for Pharmaceutical Additives, 2nd Edition (eds. M. Ash and I. Ash), 2001 (Synapse Information Resource Inc., Endicott, New York, USA).
Handbook of Pharmaceutical Excipients, 2nd edition, 1994.
Jung, C., et al., *Neuroscience Letters*, 304(3), 157–160 (2001).
Kamo, N., et al., *Journal of Membrane Biology*, 49, 105–121 (1979).
Kelso, G.F., et al., *Journal of Inorganic Biochemistry*, 86, 290 (2001).
Murphy, M., *Expert Opin. Biol. Ther.*, 1(5), 753–764 (2001).
Parnham, M.J., et al., *Agents and Actions*, 27, 306–308 (1989).
*Protective Groups in Organic Synthesis*, T. Green and P. Wuts; 3rd Edition; John Wiley and Sons, (1999).
Remington's Pharmaceutical Sciences, 18th edition, Mack Publishing Company, Easton, Pa., 1990.
Rottenberg, *Methods in Enzymology*, 55, 547–560 (1979).
Rupniak, H., et al., *Neurotoxicity Research*, 2(2–3), 167–178 (2000).
Salvemini, D., et al., *Nature Reviews Drug Discovery* 1, 367–374 (2002).
Sies, H., *Adv. Pharmacol.*, 38, 229–246 (1997).
Takalo, H., et al., *Acta Chemica Scandinavica*, B 42, 373–377 (1988).
Tarino, J., *Nutrition Reports International*, 33(2), 299–306 (1986).
Kelso, G.F. et al., "Understanding the Role of Superoxide in Mithochrondrial Biology Using a Triphenylhosphoneum Modified Manganese (II) SOD Mimic," Poster Presentation at 10th International Conference on Bioinorganic Chemistry (Aug. 26–31, 2001) Florence, Italy.
Muller, A. et al., "A Novel Biologically Active Seleno–Organic Compound–1. Glutathione Peroxidase–Like Activity *in Vitro* and antioxdant Capacity of PZ 51 (Ebselen)," Biochemical Pharmacology, (1984) 33:20:3235–3239.
Namura, S. et al., "Ebselen Redduces Cytochrome c Release From Mitochondria and Subsequent DNA Fragmentation After Transient Focal Cerebral Ischemia in Mice," Stroke. (2001) 32:8:1906–1911.
Vogel's Textbook of Practical Organic Chemistry, 5th edition, Ed. Furniss, B.S., Hannaford, A.J., Smith, P.W.G., Tatchell, A.R., Longman, UK (1996) (Book —Not Provided).

* cited by examiner

Primary Examiner—Elvis O. Price
Assistant Examiner—Michael C. Henry
(74) Attorney, Agent, or Firm—Michael Best & Friedrich, LLP (57) ABSTRACT

The invention provides mitochondrially targeted antioxidant compounds comprising a lipophilic cation moiety covalently coupled to an antioxidant moiety which is either a superoxide dismutase (SOD) mimetic or a glutathione peroxidase mimetic. These compounds can be used to treat patients who would benefit from the reduction of oxidative stress.

11 Claims, 2 Drawing Sheets

MITOCHONDRIALLY TARGETED ANTIOXIDANTS

The present invention relates to compounds which are mitochondrially targeted antioxidants, their use and synthesis.

Mitochondria are intracellular organelles responsible for energy metabolism. Consequently, mitochondrial defects are damaging, particularly to neural and muscle tissues which have high energy demands.

Mitochondrial dysfunction is central to a number of human degenerative diseases, and can be due to primary defects in genes encoded by mitochondrial DNA, by mutations in nuclear encoded genes, or due to secondary consequences of other defects. Oxidative damage to the mitochondrion is a major factor in the pathophysiology of these diseases, because the mitochondrial respiratory chain is the major source of reactive oxygen species (ROS) within most human cells. These diseases include Parkinson's disease, Friedreich's Ataxia, Wilson's Disease, mtDNA diseases, diabetes, motor neurone disease and the non-specific loss of vigour associated with ageing. Oxidative damage to mitochondria also contributes to the pathophysiology of inflammation and ischaemic-reperfusion injury in stroke, heart attack and during organ transplantation and surgery.

To prevent the damage caused by oxidative stress a number of antioxidant therapies have been developed. In addition, a range of therapeutically or prophylactically useful compounds designed to protect or alter mitochondrial function have been designed. The present inventors have previously disclosed (WO 99/26954) that certain classes of antioxidants can be targeted to mitochondria by their covalent attachment to lipophilic cations by means of alkylene chain. In particular, the targeting of Vitamin E and Ubiquinol to mitochondria by linking them to the triphenyl phosphonium ion was described.

The present invention relates to the targeting of two classes of antioxidant moieties to mitochondria by their attachment to lipophilic cation moieties.

The antioxidant moieties which have been previously targeted to mitochondria are to some extent destroyed when removing reactive oxygen species, in that although the active antioxidant moiety may be regenerated to some degree by processes occurring in the mitochondria or the cell, the regeneration processes produce by-products, eventually leading to a complete loss or severe reduction of antioxidant function. To overcome this reduction in function, the antioxidant compounds must be replenished over time or be present in sufficient quantity so as to avoid a loss of efficacy of the treatment.

A first aspect of the present invention provides a compound comprising a lipophilic cation moiety covalently coupled to an antioxidant moiety which is a superoxide dismutase (SOD) mimetic.

Preferably the SOD mimetic moiety comprises at least one manganese atom in either oxidation state II or III. Preferred classes of manganese based SOD mimetics include Mn III metalloporphyrins, Mn II-salen complexes and Mn II-pentaazamacrocyclic ligand-based compounds. Such compounds are disclosed in Salvemini, D., et al., *Nature Reviews Drug Discovery* 1, 367–374 (2002), which is incorporated herein by reference.

Compounds of this aspect therefore have the following structure:

where L is a linking group and Z is an anion, and preferably a pharmaceutically acceptable anion.

A second aspect of the present invention provides a compound comprising a lipophilic cation moiety covalently coupled to an antioxidant moiety which is a glutathione peroxidase mimetic.

Preferably the glutathione peroxidase mimetic is a selenoorganic compound, i.e. an organic compound comprising at least one selenium atom. Preferred classes of selenoorganic glutathione peroxidase mimetics include benzisoselenazolones, diaryl diselenides and diaryl selenides. Such compounds, are disclosed in: Sies, H., *Adv. Pharmacol.*, 38, 229–246 (1996); Galet, V., et al., *J. Med. Chem.*, 37, 2903–2911 (1994); Parnham, M. J., et al., *Agents and Actions*, 27, 306–308; Andersson, C-M., et al., *Free Radical Biol. & Med.*, 16, 17–28 (1994); Chaudiere, J, et al., "Design of New Selenium-Containing Mimics of Glutathione Peroxidase", 165–184, in *Oxidative Processes and Antioxidants*, edited by R. Paoletti, et al., Raven Press, New York (1994), which are incorporated herein by reference.

Compounds of this aspect therefore have the following structure:

where L is a linking group and Z is an anion, and preferably a pharmaceutically acceptable anion.

A third aspect of the present invention provides a compound of the first or second aspects for use in methods of treatment of the human or animal body.

A fourth aspect of the present invention provides a pharmaceutical composition comprising a compound of the first or second aspects in combination with one or more pharmaceutically acceptable carriers or diluents.

A fifth aspect of the present invention provides a method of treatment of a patient who would benefit from reduced oxidative stress which comprises the step of administering to said patient a therapeutically effective amount of a compound of the first or second aspects.

In a further aspect, the present invention provides a method of reducing oxidative stress in a cell which comprises the step of administering to said cell a compound of the first or second aspect.

Another aspect of the present invention provides the use of a compound of the first or second aspects for the manufacture of a medicament for use in the treatment of a condition ameliorated by reduced oxidative stress.

Conditions ameliorated by reduced oxidative stress include Parkinson's disease, Friedreich's Ataxia, Wilson's Disease, mtDNA diseases, diabetes, motor neurone disease, inflammation and ischaemic-reperfusion tissue injury in strokes, heart attacks, organ transplantation and surgery.

Preferred features of the invention will be now be described by way of further definition and example, with reference to the following figures.

Lipophilic Cation Moieties

Mitochondria have a substantial membrane potential of up to 180 mV across their inner membrane (negative inside). Because of this potential, membrane permeant, lipophilic cations accumulate several-hundred fold within the mitochondrial matrix. (Rottenberg, *Methods in Enzymology,* 55, 547–560 (1979); Chen, *Ann. Rev. Cell Biol.,* 4, 155–181 (1988)). Such ions are accumulated provided they are sufficiently lipophilic to screen the positive charge or delocalise it over a large surface area, also provided that there is no active efflux pathway and the cation is not metabolised or immediately toxic to a cell.

The lipophilic cation moieties of the present invention may be ammonium, phosphonium or arsonium cations, and in particular tribenzyl or triphenyl substituted cation moieties, of which the phenyl groups may be optionally substituted, for example hydroxy (OH), alkoxy (O—$C_{1-7}$ alkyl), nitro ($NO_2$), amido ($CONH_2$), carboxy (COOH) or $C_{1-7}$ alkyl, at one or more of the 3-, 4- and 5-positions. Examples include, but are not limited to, tribenzyl ammonium, tribenzyl phosphonium, tribenzyl arsonium, and triphenyl phosphonium cations. Of these triphenyl phosphonium is preferred.

The lipophilic cation moieties may also be fluorescent or light absorbing. Examples include, but are not limited to, rhodamine 123, JC-1, N,N'-bis(2-ethyl-1,3-doxylene) kryptocyanine, pyronine Y, o-toluidine blue, chalcogenpyrilium and benzo(a)phenoxazinium (see Chen, L., *Ann. Rev. Cell Biol.,* 4, 155–181 (1988), which is incorporated herein by reference).

Triphenyl phosphonium is the most preferred lipophilic cation moiety for the present invention.

SOD Mimetic Moieties

Naturally occurring superoxide dismutase (SOD) enzymes are metalloproteins that use an efficient dismutation as a mechanism to detoxify superoxide ($O_2.^-$) anions. SOD mimetics are chemical entities which copy the functional properties of these enzymes. In common with some naturally occurring enzymes, it is preferred that the SOD mimetic comprises at least one manganese atom in either oxidation state II or III, although other transition metal ions, in particular iron and copper, may be suitable in place of manganese.

A number of classes of manganese based SOD mimetics are disclosed in Salvemini, D., et al., *Nature Reviews Drug Discovery* 1, 367–374 (2002), and these include Mn III metalloporphyrins, Mn II-salen complexes and Mn II-pentaazamacrocyclic ligand-based compounds.

Metalloporphyrins are metal complexes with a porphyrin ligand, which is a completely unsaturated macrocyclic tetrapyrrole ligand that contains a n-conjugated ring system. An example of this class of SOD mimetic is Mn III tetrakis-(4-benzoic acid)porphyrin (MnTBAP).

Mn II-salen(salicylaldehyde-ethylenediamine Schiff's base adduct) complexes (Mn II-salen complexes) have been reported to be SOD mimetics, and include EUK-8 (Chloro (bis(salicylidene)ethylenediamine)manganese) and EUK134 (Phenol, 2,2'-[1,2-thanediylbis (nitrilomethylidyne)]bis[6-methoxy-, manganese complex), see Jung, C., et al., *Neuroscience Letters,* 304(3), 157–160 (2001) and Rupniak, H., et al., *Neurotoxicity Research,* 2(2–3), 167–178 (2000), which are incorporated herein by reference.

Mn II-pentaazamacrocyclic ligand-based compounds are exemplified by the following compound (M40403):

which is a derivative of the 15-membered macrocyclic ligand 1,4,7,10,13-pentaazacyclopentadecane which contains added bis(cyclohexyl)pyridine functionalities.

Mn II-pentaazamacrocyclic ligand-based moieties are the preferred class of Mn-based SOD mimetics, with M40403 being the most preferred.

Glutathione Peroxidase Mimetic Moieties

Glutathione peroxidase reduces hydrogen peroxide to water, and organic hydroperoxides to alcohol, whilst oxidising glutathione to glutathione disulphide. It is known that glutathione peroxidase has selenium as an integral part of its active site. It is therefore preferred that glutathione peroxidase mimetics are selenoorganic compounds, i.e. organic compounds comprising at least one selenium atom.

A number of classes of selenoorganic glutathione peroxidase mimetics have been disclosed in the references given above, and include benzisoselenazolones, diaryl diselenides and diaryl selenides.

Benzisoselenazolones have the general structure:

where R can be a variety of alkyl and aryl groups. The benzene ring can bear substituents, and can also be replaced by other fused aromatic rings, for example, pyridine. The most extensively studied, and preferred, member of this class is Ebelsen (2-phenyl-benzo[d]isoselenazol-3-one):

Diaryl diselenides are of the general formula:

where the term "aryl", as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

The ring atoms may be all carbon atoms, as in "carboaryl groups", for example those derived from benzene (i.e. phenyl) ($C_6$) and naphthalene ($C_{10}$), or the ring atoms may include one or more heteroatoms, as in "heteroaryl groups", for example those derived from pyridine ($C_6$), furan ($C_5$), thiophene ($C_5$) and pyrimidine ($C_6$).

Preferably the aryl groups are optionally substituted phenyl groups.

Examples of this class of compound include bis(2-amino) phenyl diselenide and bis(2-amino, 5-acetyl)phenyl diselenide.

Diaryl selenides are of the general formula:

where the term "aryl" is as defined above. Preferably the aryl groups are optionally substituted phenyl groups.

Examples of this class of compound include di(4-aminophenyl) selenide and di(4-phenylphenyl) selenide.

Benzisoselenazolones are the preferred class of selenoorganic glutathione peroxidase mimetics, with Ebelsen being the most preferred.

Covalent Linking Groups

The covalent linking group may be any group which joins the lipophilic cation moiety to the enzyme mimetic with a covalent bond at each end, and enables the two moieties to remain bonded together while crossing the mitochondrial inner membrane into the mitochondrial matrix.

Typically the group will be an alkylene group. The term "alkylene," as used herein, pertains to a bidentate moiety obtained by removing two hydrogen atoms, either both from the same carbon atom, or one from each of two different carbon atoms, of a hydrocarbon compound having from 1 to 30 carbon atoms, which may be aliphatic or alicyclic, and which may be saturated, partially unsaturated, or fully unsaturated. Thus, the term "alkylene" includes the subclasses alkenylene, alkynylene, cycloalkylene, etc., discussed below.

In this context, the prefixes (e.g. $C_{1-4}$, $C_{1-7}$, $C_{1-30}$, $C_{2-7}$, $C_{3-7}$, etc.) denote the number of carbon atoms, or range of number of carbon atoms. For example, the term "$C_{1-4}$ alkylene" as used herein, pertains to an alkylene group having from 1 to 4 carbon atoms. Examples of groups of alkylene groups include $C_{1-4}$ alkylene ("lower alkylene"), $C_{1-7}$ alkylene, and $C_{1-30}$ alkylene.

Examples of linear saturated $C_{1-7}$ alkylene groups include, but are not limited to, —$(CH_2)_n$— where n is an integer from 1 to 7, for example, —$CH_2$— (methylene), —$CH_2CH_2$— (ethylene), —$CH_2CH_2CH_2$— (propylene), and —$CH_2CH_2CH_2CH_2$— (butylene).

Examples of branched saturated $C_{1-7}$ alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{1-7}$ alkylene groups include, but are not limited to, —CH=CH— (vinylene), —CH=CH—$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—$CH_2$—CH=CH—, —CH=CH—$CH_2$—$CH_2$—CH=CH—, —$CH_2$—CH=CH—, and —CH=CH—$CH_2$—$CH_2$—CH=CH—.

Examples of branched partially unsaturated $C_{1-7}$ alkylene groups include, but are not limited to, —$C(CH_3)$=CH—, —$C(CH_3)$=CH—$CH_2$—, and —CH=CH—CH($CH_3$)—.

Examples of alicyclic saturated $C_{1-7}$ alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

The alkylene group may be substituted by substituent groups that increase the solubility of the molecule, increase the uptake of the molecule across the mitochondrial membrane, or decrease the rate of degradation of the molecule in vivo. In particular, the linking group may be substituted by: hydroxy groups, which have the formula —OH; thio groups, which have the formula —SH; amino groups, which have the formula —$NH_2$; carboxy groups, which have the formula —C(=O)OH; amido groups, which have the formula —C(=O)$NH_2$; or groups derived from sugars or sugar derivatives.

The hydroxy, thio, amino, carboxy and amido groups are preferred located at the end of branches in the linking group, so that the overall effect is that of an alcohol, thiol, amine, carboxylic acid or amide respectively attached at one end to the backbone of the linking group.

Sugars (saccharides) are carbohydrates which can be considered to be hydroxylated aldehydes and ketones. If two or more monosaccharides are linked, for example, via an acetal linkage, the compound is conventionally referred to as a disaccharide (e.g. sucrose, maltose), trisaccharide, etc., and these may all be used in the invention. Polysaccharides are not intended for use in the present invention.

Monosaccharides are conventionally named according to the overall number of carbon atoms, for example, tri- ($C_3$), tetr- ($C_4$), pent- ($C_5$), and hex- ($C_6$). Monosaccharides may be in, for example, aldose, ketose, aldoketose, and dialdose form. Aldoses are conventionally named as -ose, for example, triose ($C_3$), tetrose ($C_4$), pentose ($C_5$), hexose ($C_6$), and heptose (C). Ketoses are conventionally named as -ulose, for example, tetrulose ($C_4$), pentulose ($C_5$), hexulose ($C_6$), and heptulose (C7). Aldoketoses are conventionally named as -osulose. Dialdoses are conventionally named as -odialdose. Monosaccharides may have one or more chiral centres, and thus may have different stereoisomeric forms (e.g., R-, S-, D-, L-, α-, β-, (+), (−), and combinations thereof, e.g., α-D-, β-D-, α-L-, β-L-). Isomers which are superimposable mirror images are conventionally referred to as enantiomers. Isomers which differ from each other by the configuration at two or more chiral centres are conventionally referred to as diasteriomers. Isomers which differ from each other by the configuration at only one chiral centre are conventionally referred to as epimers (e.g., D-ribose and D-xylose).

The configuration at each chiral centre is conventionally denoted R or S. The prefixes D- or L- are conventionally used to indicate monosaccharides with a configuration that is related to D- and L-glyceraldehyde, respectively. The prefixes (+)- and (−)- are conventionally used to indicated monosaccharides which are dextrorotatory (rotate the plane of polarised light to the right, in a clockwise direction) or levorotatory (to the left, in a counter-clockwise direction).

The prefixes erythro- and threo- denote certain tetrose ($C_4$) diasteriomers. The prefixes arabino-, lyxo-, ribo-, and xylodenote certain pentose ($C_5$) diasteriomers. The prefixes allo-, altro-, gluco-, manno-, gulo-, ido-, galacto-, and talodenote certain hexose ($C_6$) diasteriomers.

In cyclic form (hemiacetal or hemiketal form), monosaccharides are conventionally named according to the number of ring atoms. For example, a furanose has a 5-membered ring; a pyranose has a 6-membered ring; a septanose has a 7-membered ring. The prefixes α- and β- are conventionally used to indicate the two anomers which arise from the new chiral centre which is formed upon cyclisation.

Examples of saccharides include, but are not limited to, the following, which may be in a α-D, β-D, α-L, or β-L form:

erythrose and threose;

arabinose, lyxose, ribose, and xylose;

allose, altrose, glucose, mannose, gulose, idose, galactose, and talose;

arabinofuranose, lyxofuranose, ribofuranose, and xylofuranose;

allofuranose, altrofuranose, glucofuranose, mannofuranose, gulofuranose, idofuranose, galactofuranose, talofuranose;

allopyranose, altropyranose, glucopyranose, mannopyranose, gulopyranose, idopyranose, galactopyranose, and talopyranose.

Many saccharides are known by their trivial names, for example, D-threose (D-threo-tetrose), D-ribose (D-ribopentose), D-galactose (D-galacto-hexose), D-fructose (D-arabino-2-hexulose), L-sorbose (L-xylo-2-hexulose), D-ribulose (D-erythro-2-pentulose), D-sedoheptulose (D-altro-2-heptulose).

Many saccharides derivatives are well known, for example, deoxy-saccharides (e.g., 6-deoxy-L-galactose, also known as L-fucose; 6-deoxy-L-mannose, also known as L-rhamnose; 2-deoxy-D-erythro-pentose, also known as deoxyribose or 2-deoxy-D-ribose); glycosides (e.g., methyl α-D-glucopyranoside); amino-deoxy-saccharides, also known as glucosamines (e.g., D-glucosamine, D-galactosamine); alditols (e.g., D-glutitol, also known as D-sorbitol; D-mannitol; meso-galactitol); aldonic acids, also known as glyconic acids (e.g., D-gluconic acid); uronic acids, also known as glycouronic acids (e.g., D-galactouronic acid); and aidaric acids, also known as glycaric acids (e.g., L(+)-tartaric acid).

The alkylene group may have a heteroatom, selected from O, S or NH at its end adjacent the enzyme mimetic moiety.

Preferred linking groups are $C_{1-30}$ alkylene groups, more preferably $C_{1-20}$, $C_{1-10}$ or $C_{1-4}$ alkylene groups, optionally terminating at the enzyme mimetic end with an O or S, for example —S—$(CH_2)_3$— and —O—$(CH_2)_4$—.

The linking group is preferably attached to the enzyme mimetic moiety on an aromatic ring, for example a benzene or pyridine ring.

Anions

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous

Examples of suitable organic anions include, but are not limited to, those derived from the following organic acids: tetraphenylboronic, 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric.

The above anions are generally pharmaceutically acceptable. Examples of pharmaceutically acceptable salts are discussed in Berge, et al., "Pharmaceutically Acceptable Salts," *J. Pharm. Sci.*, 66, 1–19 (1977), which is incorporated herein by reference.

In the present invention inorganic anions are preferred, and in particular the halo anions, of which $Br^-$ is the most preferred.

Preferred Compounds

Preferred compounds of the first aspect of the invention have the formula:

where Z and L are as defined above, and more preferably have the formula:

where Z is as defined above, X is O, S, or NH, and preferably O or S, and n is from 1 to 20, more preferably 3 to 6.

Preferred compounds of the second aspect have the formula:

where Z and L are as defined above, and more preferably have the formula:

where Z is as defined above, X is O, S, or NH, and preferably O or S, and n is from 1 to 20, more preferably 3 to 6.

Treatment

The term "treatment" as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount" as used herein, pertains to that amount of an active compound, or a material, composition or dosage form comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously.

The compound or pharmaceutical composition comprising the compound may be administered to a subject by any convenient route of administration, whether systemically/peripherally or topically (i.e., at the site of desired action).

While it is possible for the active compound to be used (e.g., administered) alone, it is often preferable to present it as a formulation.

Suitable carriers, diluents, excipients, etc. can be found in standard pharmaceutical texts. See, for example, Handbook for Pharmaceutical Additives, 2nd Edition (eds. M. Ash and I. Ash), 2001 (Synapse Information Resources, Inc., Endicott, N.Y., USA), Remington's Pharmaceutical Sciences, 18th edition, Mack Publishing Company, Easton, Pa., 1990; and Handbook of Pharmaceutical Excipients, 2nd edition, 1994, which are incorporated herein by reference.

The term "pharmaceutically acceptable" as used herein pertains to compounds, ingredients, materials, compositions, dosage forms, etc., which are, within the scope of sound medical judgment, suitable for use in contact with the tissues of the subject in question (e.g. human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier +which constitutes one or more accessory ingredients. In general, the formulations are prepared by uniformly and intimately bringing into association the active compound with carriers (e.g. liquid carriers, finely divided solid carrier, etc.), and then shaping the product, if necessary.

It will be appreciated by one of skill in the art that appropriate dosages of the compounds, and compositions comprising the compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 1 $\mu$g to about 250 mg per kilogram body weight of the subject per day.

Further Uses

The compounds of the first and second aspects may also be useful for perfusing isolated organs prior to transport, and in storing frozen cells, for example, embryos.

Synthesis Routes

Methods for the chemical synthesis of compounds of the present invention are described herein. These methods may be modified and/or adapted in known ways in order to facilitate the synthesis of additional compounds within the scope of the present invention. The amounts of reactants given are for guidance. Descriptions of general laboratory methods and procedures, useful for the preparation of the compounds of the present invention, are described in Vogel's Textbook of Practical Organic Chemistry ($5^{th}$ edition, Ed. Furniss, B. S., Hannaford, A. J., Smith, P. W. G., Tatchell, A. R., Longmann, U K).

The synthesis of compounds of the present invention has three key steps:

(i) formation of the antioxidant moiety;
(ii) attachment of the linking group to the lipohilic cation moiety;
(iii) attachment of the linking group to the antioxidant moiety.

These three steps can be carried out in any order, which will be dependent on the methods used and the nature of each of the three groups. It is possible that the formation of the antioxidant moiety can be interrupted by linking a precursor to the linking group. If necessary, protecting groups can be employed to avoid any unwanted reactions occurring during the synthesis (see *Protective Groups in Organic Synthesis*, T. Green and P. Wuts; 3rd Edition; John Wiley and Sons, 1999).

Formation of the antioxidant moiety: this will depend on the nature of the antioxidant moiety, and can usually be based on the disclosed routes for forming that moiety. It is sometimes convenient to synthesise the enzyme mimetic moiety with the heteroatom (O, S or NH) that is on the end of the alkylene chain of the linking group adjacent the moiety, to aid the joining of the linking group to the enzyme mimetic moiety.

Linking the linking group to the lipophilic cation moiety: it is generally preferred to carry this step out by heating a halogenated precursor, preferably an iodinated or brominated precursor (RBr or RI), sometimes in an appropriate solvent with 2–3 equivalents of the lipophilic cation precursor under argon for several days. R can either be the linking group, the linking group already attached to the enzyme mimetic moiety, or the linking group attached to a precursor of the enzyme mimetic moiety. The compound is then isolated as its bromide or iodide salt. To do this the solvent is removed (if necessary), the product is then triturated repeatedly with a compound such as diethyl ether, until an solid remains. This can then be dissolved in a solvent, e.g. dichloromethane, and precipitated with diethyl ether to remove the excess unreacted cation. This can be repeated. Purification can involve recrystallisation, for example, from methylene chloride/diethyl ether or chromatography on silica gel eluting with dichloromethane/ethanol mixtures.

Linking the linking group to the antioxidant moiety: this will depend on the nature of the antioxidant moiety. One method of achieving this linking is to synthesise the linking group as part of the antioxidant moiety. Alternatively, if the antioxidant moiety has been synthesised with a heteroatom in place (see above), then the linking group can be joined by treating the antioxidant moiety with a strong base and reacting it with the linking group having a suitable leaving group (for example, halo).

EXAMPLES

General Experimental Details

Preparative column chromatography was performed using silica gel (Merck) type 60, 200–400 mesh, 40–63 um. Analytical thin layer chromatography (TLC) was performed using silica gel (Merck) 60F 254 coated on alumina roll and visualization accomplished with UV light. Nuclear magnetic resonance spectra were acquired using a Varian 300 MHz instrument. Tetramethylsilane was used as an internal standard for $^1H$ and $^{13}C$ NMR experiments in $CDCl_3$, and 85% phosphoric acid was used as an internal standard for $^{31}P$ NMR experiments in all solvents. Residual solvent peaks were used as internal standards in $^1H$ and $^{13}C$ NMR experiments not performed in $CDCl_3$. Chemical shift ($\delta$) data are reported in units of ppm relative to the internal standard. Peak assignment for $^{13}C$ NMR were made on the basis of chemical shift, relative intensity and HSQC data. Infrared absorption spectra were acquired using a Perkin Elmer Spectrum BX FTIR instrument. Samples were examined as KBr discs prepared using anhydrous KBr and units of absorption are reported in wavenumbers ($cm^{-1}$). Low resolution electrospray (LRES) and low resolution atmospheric pressure chemical ionisation (LRAPCI) mass spectra were acquired using a Shimadzu LCMS-QP800X liquid chromatograph mass spectrometer and data are reported as m/z values. Melting points were acquired using a Kofler Heizbank melting point bench and are reported uncorrected. Synthesis of Manganese(II) dichloro((4R, 9R, 14R, 19R)-24-(3-triphenylphosphoniopropane-1-thio)-3, 10, 13, 20, 26-pentaazatetracyclo[20.3.1.0.$^{4,9}$. $0^{14,19}$]hexacosa-[(26),-22(23),24-triene) chloride (Compound 9)

N,N'-Bis{(1R,2R)-[2-(amino)]cyclohexyl}-1,2-diaminoethane tetrahydro chloride (1) was prepared as reported in the literature (U.S. Pat. No. 6,214,817, which is incorporated herein by reference).

4-(3-triphenylphosphoniopropane-1-thio)-2,6-diformylpyridinebromide (Compound 8) was prepared as follows and as shown in scheme 2.

Dimethyl-4-bromo-2,6-pyridinedicarboxylate (Compound 2) A mixture of chelidamic acid monohydrate (8.42 g, 41.87 mmol) and PBr$_5$ (93 g) in a dry Shlenk tube equipped with a reflux condenser was heated under a nitrogen atmosphere to 120° C. A melt formed which was stirred under a nitrogen atmosphere for 3 hours at 100° C. The resultant purple melt was cooled to room temperature and transferred to a round bottom flask equipped with a drying tube by washing with CHCl$_3$ (3×50 mL). The solution was cooled to 0° C. and dry MeOH (150 mL) was slowly added. The resultant brown solution was stirred overnight and then concentrated in vacuo to a slurry. Solid was recrystallised from MeOH (175 mL), filtered, washed with ice cold MeOH (3×50 mL) and sucked dry, giving 2 as white needles (8.29 g, 72%) $^1$H NMR (299.9 MHz, CDCl$_3$) δ 8.46 (s, 2H, Ar—H), 4.04 (s, 6H, —OCH$_3$) ppm; $^{13}$C NMR (125.7 MHz, CDCl$_3$) δ 164.36 (carbonyl), 149.42 (aromatic), 135.37 (aromatic), 131.66 (protonated aromatic), 53.83 (methyl) ppm; Anal. Calcd. for C$_9$H$_8$NO$_4$Br: C: 39.43, H: 2.94, N: 5.11, Found: C: 39.68, H: 2.92, N: 5.09; m.p. 166–167° C.

4-Bromo-2,6-pyridinedimethanol (Compound 3)

To an ice cold slurry of 2 (10.0 g, 36.5 mmol) in MeOH (230 mL) under an argon atmosphere was added NaBH$_4$ (6.2 g, 164 mmol) in small portions over 1 hour. The resultant pale yellow solution was stirred under argon at 0° C. for 1 hour, room temperature for 3 hours and under reflux overnight. Acetone (40 mL) was then added and the solution was refluxed a further 1 hour. The solution was cooled and concentrated in vacuo to an oily residue. The residue was taken up in sat. Na$_2$CO$_3$ (65 mL) and the suspension brought to reflux. Water was added in 10 mL portions until all solids had dissolved under reflux (~120 mL H$_2$O). The solution was left to cool and sit at room temperature overnight. The resultant suspension was filtered and the precipitate washed with CHCl$_3$ (30 mL), and sucked dry. The filtered material was taken up in THF (90 mL), the suspension brought to boiling and filtered hot. The filtrate was collected and solvent removed in vacuo to give 3 as a white solid (5.92 g, 74%). $^1$H NMR (299.9 MHz, d$_6$-DMSO) δ 7.55 (t, J$_{allylic}$= 0.75 Hz, 2H, Ar—H), 5.57 (t, J=6 Hz, 2H, C—OH), 4.56 (d, J=6 Hz, 4H, Ar—CH$_2$—) ppm; $^{13}$C NMR (125.7 MHz, d$_6$-DMSO) δ 164.16 (aromatic), 134.17 (aromatic), 121.98 (protonated aromatic), 64.57 (methylene) ppm; m.p. 164° C., lit. (Takalo, H., et al., *Acta Chemica Scandinavica*, B 42, 373–377 (1988)) 162–164° C.

4-Bromo-2,6-diformylpyridine (Compound 4)

A mixture of 3 (4.00 g, 18.35 mmol), silica gel (3.51 g, 200–400 mesh, 40–63 μm) and 4-acetylamino-2,2,6,6-tetramethylpiperidine 1-oxoammonium tetrafluoroborate (prepared as reported in the literature, Bobbit, J. M., *J. Org. Chem.*, 63, 9367–9374 (1998), which is incorporated herein by reference) (11.78 g, 39.25 mmol) in CH$_2$Cl$_2$ (230 mL) was stirred under a nitrogen atmosphere for 2 days. The slurry was filtered through a plug of silica and the filtered material washed with CH$_2$Cl$_2$ until TLC analysis (EtOac/ 10% MeOH/1% ET$_3$N) showed all product had been eluted (5×40 mL). The fractions containing product were combined and solvent removed in vacuo to give 4 as a pale yellow solid (2.41 g, 61%). $^1$H NMR (299.9 MHz, CDCl$_3$) δ 10.12 (s, 2H, —CH=O), 8.30 (s, 2H, Ar—H) ppm; $^{13}$C NMR (125.7 MHz, CDCl$_3$) δ 191.41 (—CH=O), 154.02 (aromatic), 136.02 (aromatic), 128.80 (protonated aromatic); Anal. calcd. for C$_7$H$_4$NO$_2$Br: C: 39.28, H: 1.88, N: 6.54, Found: C: 39.55, H: 1.79, N: 6.41.

4-Bromo-2,6-bis(1,3-dioxolan-2-yl)pyridine (Compound 5)

A mixture of 4 (800 mg, 3.74 mmol), ethylene glycol (4.64 g, 74.6 mmol) and p-toluenesulfonic acid (46 mg, 0.270 mmol) in dry toluene (50 mL) was refluxed under an argon atmosphere for 24 hours in flask equipped with a Dean-Stark apparatus. After this time TLC analysis (9:1 CH$_2$Cl$_2$/EtOAc) showed no starting material to be present. The mixture was then cooled and washed with 10% Na$_2$CO$_3$ (2×50 mL), and water (2×50 mL). The organic phase was dried over Na$_2$SO$_4$ and filtered. Solvent was removed from the filtrate in vacuo, giving a pale yellow oil. The oil was refrigerated overnight, giving sufficiently pure 5 as a tan solid (974 mg, 86%). $^1$H NMR (299.9 MHz, CDCl$_3$) δ 7.72 (s, 2H, Ar—H), 5.85 (s, 2H, methine), 4.12 (m, 8H, —O—CH$_2$—CH$_2$—O—); $^{13}$C NMR (125.7 MHz, CDCl$_3$) δ 158.56 (aromatic), 134.66 (aromatic), 124.63 (protonated aromatic), 103.21 (methine), 65.98 (methylene); LRAPCI MS (+formic acid) Calcd. For C$_{11}$H$_{13}$NO$_4$Br: 302, 304 found 302, 304.

4-(3-hydroxypropane-1-thio)-2,6-bis(1,3-dioxolan-2-yl) pyridine (Compound 6)

A solution of 3-mercapto-1-propanol (450 mg, 4.88 mmol) in dry DMF (20 mL) under an argon atmosphere was added to solid NaH (198 mg 60% emulsion washed with hexane and dried in vacuo, 4.96 mmol) under an argon atmosphere via a cannula. The mixture was stirred under argon until a solution formed and effervescence ceased. The thiolate solution was then added via a cannula to an ice-cold solution of 5 (905 mg, 3.00 mmol) in dry DMF (20 mL) under an argon atmosphere. The resultant pale brown solution was stirred under an argon atmosphere for 2 hours at 0° C. and at room temperature for 20 hours. Water (5 mL) was carefully added and most of the solvent was then removed in vacuo, giving a brown oil. The oil was extracted with $CH_2Cl_2$ (75 mL) and the organic extract washed with water (3×50 mL), dried over $Na_2SO_4$ and filtered. Solvent was removed from the filtrate in vacuo to give an oily residue, which solidified upon cooling. The crude solid was recrystallised from EtOAc containing a few drops of $CHCl_3$. The crystals were filtered, washed with diethyl ether and sucked dry, giving 6 as white crystals (616 mg). An additional amount of product (105 mg) was recovered by chromatography of the filtrate (silica gel packed in $CH_2Cl_2$, eluting with 99:1 $CH_2Cl_2$/MeOH (10 mL), 49:1 $CH_2Cl_2$/MeOH (10 mL), 97:3 $CH_2Cl_2$/MeOH (10 mL), 19:1 $CH_2Cl_2$/MeOH (10 mL). The combined yield was 721 mg (77%). $^1$H NMR (299.9 MHz, $CDCl_3$) δ 7.40 (s, 2H, Ar—H), 5.83 (s, 2H, methine), 4.1 (m, 8H, —O—$CH_2$—$CH_2$—O—), 3.78 (t, J=5.9 Hz, 2H, —$CH_2$—OH), 3.16 (t, J=7.2 Hz, 2H, —S—$CH_2$—), 1.95 (dt, 2H, —$CH_2$—$CH_2$—$CH_2$—); $^{13}$C NMR (125.7 MHz, $CDCl_3$) δ 156.68 (aromatic), 151.77 (aromatic), 117.88 (protonated aromatic), 103.62 (methine), 65.88 (—O—$CH_2$—$CH_2$—O), 61.23 (—$CH_2$—OH), 31.52 (—$CH_2$—$CH_2$—$CH_2$—), 27.47 (—S—$CH_2$—); Anal. Calcd. for $C_{14}H_{19}NO_5S$: C: 53.66, H: 6.11 N: 4.47, S:10.23, found: C: 53.41, H:6.17, N: 4.45, S:10.05; m.p. 74–76° C.

4-(3-bromopropane-1-thio)-2,6-diformylpyridine (Compound 7)

To a flask containing conc. HBr (7.5 g) was slowly added conc. $H_2SO_4$ (4 mL). Solid 6 (300 mg, 0.957 mmol) was added and the solution refluxed under a nitrogen atmosphere for 3 hours. After this time TLC analysis (silica, $CH_2Cl_2$) showed no starting material to be present. The solution was cooled and slowly added to sat. $NaHCO_3$ (100 mL). An additional 50 mL of sat. $NaHCO_3$ was added to give a basic suspension. The suspension was extracted with $CH_2Cl_2$ (3×50 mL), the extracts combined, dried over $Na_2SO_4$ and filtered through a plug of silica. Solvent was removed from the filtrate in vacuo to give sufficiently pure 7 as a pale yellow solid (247 mg, 89%). $^1$H NMR (299.9 MHz, $CDCl_3$) δ 10.11 (s, 2H, —CH=O), 7.95 (s, 2, Ar—H), 3.56 (t, J=6.2, 2H, —$CH_2$—Br), 3.29 (t, J=7.2 Hz, 2H, —S—$CH_2$—), 2.28 (dt, 2H, —$CH_2$—$CH_2$—$CH_2$—); $^{13}$C NMR (125.7 MHz, $CDCl_3$) δ 192.53 (—CH=O), 153.32 (aromatic), 152.85 (aromatic), 121.82 (protonated aromatic), 31.44 (—$CH_2$—Br), 31.09 (—$CH_2$—$CH_2$—$CH_2$—), 29.42 (—S—$CH_2$—); LRAPCI MS (+formic acid) Calcd. For $C_{10}H_{11}NO_2SBr$: 288, 290, found: 588, 290.

4-(3-triphenylphosphoniopropane-1-thio)-2,6-diformylpyridine bromide (Compound 8)

Triphenylphosphine (1.18 g, 4.50 mmol) and 7 (130 mg, 0.451 mmol) were placed in a dry Kimax tube. The tube was purged with argon, sealed, placed in the dark, and the mixture then stirred as a melt at 85° C. for 17 hours. The melt was cooled and the resultant solid residue dissolved in $CH_2Cl_2$ (3 mL). Product was triturated with diethyl ether (40 mL) and washed with diethyl ether (6×40 mL). Residual solvent was removed from the solid in vacuo, giving crude sufficiently pure 8 as a pink solid (248 mg, 100%). $^1$H NMR (299.9 MHz, $CDCl_3$) δ 10.15 (s, 2H, —CH=O), 7.98 (s, 2H, Ar—H), 7.90–7.60 (m, 15H, —P$^+$Ph$_3$), 4.32 (m, 2H, —$CH_2$—P'—), 3.74 (m, —S—$CH_2$—), 2.06 (—$CH_2$—$CH_2$—); $^{13}$C NMR (125.7 MHz, $CDCl_3$) δ 192.52 (—CH=O), 153.05 (aromatic), 152.82 (aromatic) 135.42 (d, J=5.03 Hz, —P$^+$Ph$_3$ para), 133.92 (d, J=16.34 Hz, —P$^+$Ph$_3$, meta), 130.79 (d, 21.34 Hz, —P$^+$Ph$_3$ ortho), 122.89 (protonated aromatic), 118.14 (d, J=145.81 MHz, —P$^+$Ph$_3$ ipso), 30.78 (d, J=32.68 Hz, —S—$CH_2$—), 22.16 (d, J=3.77 Hz, —$CH_2$—$CH_2$—$CH_2$—), 22.08 (d, J=84.22 MHz, —$CH_2$—P$^+$—); $^{31}$P NMR (121.4 MHz, $CDCl_3$) δ 25.02; LRES$^+$MS: calc. for $C_{28}H_{25}NO_2SP$: 470.1, found: 470.1.

Manganese(II) dichloro((4R, 9R, 14R, 19R)-24-(3-triphenylphosphoniopropane-1-thio)-3, 10, 13, 20, 26-pentaazatetracyclo[20.3.1.0.$^{4,9}$.0$^{14,19}$]hexacosa-1 (26),-22(23),24-triene) chloride (Compound 9)

To a slurry of 1 (200 mg, 0.363 mmol) in dry EtOH (5 mL) under an argon atmosphere was added diisopropylamine (147 mg, 1.45 mmol). The resultant solution was stirred for 30 min and $MnCl_2$ was added. A solution formed and was stirred for 1 hour. Solid 8 was added and the mixture stirred under argon for 1 hour at room temperature then at reflux for 62 hours. The mixture was cooled to 0° C. and $NaBH_4$ (55 mg, 1.45 mmol) was added in small portions over 5 h and the mixture stirred under argon for 19 hours at room temperature. Solvent was removed in vacuo and the resultant solid residue extracted with sat. NaCl (10 mL) and $CH_2Cl_2$ (10 mL). The aqueous extract was washed with $CH_2Cl_2$ (3×10 mL), the organic extracts combined, dried over $Na_2SO_4$ and filtered. Solvent was removed from the filtrate in vacuo to give a tan solid. The solid was chromatographed (silica gel packed in 99:1 $CH_2Cl_2$/MeOH, eluting with 99:1 $CH_2Cl_2$/MeOH (100 mL), 49:1 $CH_2Cl_2$/MeOH (100 mL), 19:1 $CH_2Cl_2$/MeOH (100 mL), 12:1 $CH_2Cl_2$/MeOH (100 mL), 9:1 $CH_2Cl_2$/MeOH (200 mL), 7:1 $CH_2Cl_2$/MeOH (100 mL), 17:3 $CH_2Cl_2$/MeOH (100 mL), fractions containing product were combined and solvent removed in vacuo to give a pale yellow solid. The solid was recrystallised by the slow diffusion of diethyl ether into a concentrated ethanol solution. Crystals were collected by filtration and washed with diethyl ether, giving 9 as a white solid (81 mg, 26%). This recrystallisation procedure also gave crystals of sufficient quality for x-ray diffraction analysis. LRES$^+$ MS Calcd. for [C42H55N5SPMnCl2]$^+$: 817, [C42H55N5SPMnCl]$^{2+}$: 391, [C42H55N5SPMn]$^{3+}$: 249, found: 817, 391, 249; IR: 3413 (NH stretch), 1593 (py ring vibration). X-ray diffraction data is consistent with the predicted structure.

Synthesis of 2-[4-(4-triphenylphosphoniobutoxy)phenyl]-1,2-benzisoselenazol-3(2H)-one iodide (Compound 15)

Scheme 3

N-(4-hydroxyphenyl)-benzamide (Compound 10)

A solution of benzoyl chloride (12.9 g, 91.7 mmol) in dry THF (250 mL) was added dropwise to a solution of 4-aminophenol (10.0 g, 91.7 mmol) and $Et_3N$ (9.4 g, 92.9 mmol) in dry THF (700 mL), and the mixture stirred for 2 days under a drying tube. Solvent was removed in vacuo and the solid residue extracted with $H_2O$ (3×250 mL) and diethyl ether (3×250 mL). The remaining solid material was recrystallised from aqueous ethanol, the crystals filtered, washed with diethyl ether and sucked dry, giving 10 as white crystals (14.97 g, 77%). $^1H$ NMR (299.9 MHz, $d_6$-DMSO) δ 10.06 (broad s, 1H, —OH), 9.28 (s, 1H, —NH—), 7.96 (d, J=7.8 Hz, 2H, Ar—H), 7.57 (m, 5, Ar—H), 6.78 (d, J=7.8 Hz, Ar—H); $^{13}C$ NMR (125.7 MHz, $d_6$-DMSO) δ 165.92 (carbonyl), 154.56 (aromatic), 136.09 (aromatic), 132.30 (aromatic), 131.61 (aromatic), 129.33 (protonated aromatic), 128.48 (protonated aromatic), 123.21 (protonated aromatic), 115.90 (protonated aromatic); Anal. Calcd. for $C_{13}H_{11}NO_2$: C:73.22, H: 5.20, N: 6.57, found: C: 73.33, H: 5.27, N: 6.69; m.p. 224° C.

N-[4-(tert-Butyldimethylsiloxy)phenyl]benzamide (Compound 11)

A solution of 10 (14.5 g, 68.01 mmol) and imidazole (11.6 g, 67.91 mmol) in dry THF (160 mL) was cooled to 0° C. under a drying tube. A solution of TBDMSCl in dry THF (60 mL) was added dropwise under a drying tube to the cooled solution. The resultant suspension was stirred overnight under an argon atmosphere. The suspension was then diluted with $H_2O$ (500 mL) and extracted with $CH_2Cl_2$ (2×500 mL). The organic extracts were combined, dried over $Na_2SO_4$, and filtered. Solvent was removed from the filtrate in vacuo, giving a white solid. The solid was recrystallised from hexane after a hot filtration. The crystals were collected by filtration, washed with hexane and sucked dry, giving sufficiently pure 11 as white crystals (19.86 g, 89%); $^1H$ NMR (299.9 MHz, $CDCl_3$) δ 7.86 (d, J=8.1 Hz, 1H, Ar—H), 7.85 (d, J=8.1 Hz, 1H, Ar—H), 7.57–7.44 (m, 5H, Ar—H), 6.84 (d, J=8.5 Hz, 2H, Ar—H), 0.99 (s, 9H, t-butyl methyl), 0.20 (s, 6H, methyl); $^{13}CNMR$ (125.7 MHz, $CDCl_3$) δ 165.97 (carbonyl), 152.9 (aromatic), 135.45 (aromatic), 132.04 (protonated aromatic), 131.88 (aromatic), 129.11 (protonated aromatic), 127.31 (protonated aromatic), 122.22 (protonated aromatic), 120.80 (protonated aromatic), 26.04 (methyl), 18.56 (tertiary), −4.10 (methyl); LRAPCI MS (+formic acid) Calcd. For $C_{19}H_{24}NO_2SiSe$; 328, found: 328.

2-[4-(tert-Butyldimethylsiloxy)phenyl]-1,2-benzisoselenazol-3(2H)-one (Compound 12)

To a solution of 11 (9.20 g, 28.09 mmol) in dry THF (150 mL) under argon and cooled to −15° C. was slowly added n-BuLi (1.6 M in hexane, 35 mL, 56.0 mmol) via a cannula over 45 minutes. The resultant orange solution was stirred at −15° C. for 45 minutes and selenium powder (2.22 g, 28.12 mmol) was then added. The resultant suspension was stirred for 45 minutes at −15° C., giving a deep red solution. The solution was cooled to −78° C. and $CuBr_2$ (12.55 g, 56.18 mmol) was added in 3 portions over 15 minutes. The resultant suspension was stirred for 1 h at −78° C. then removed from the cooling bath and stirred for 22 hours. The resultant brown suspension was poured into 1% aqueous acetic acid (600 mL) and extracted with $CH_2Cl_2$ (3×500 mL). The organic fractions were combined and filtered. The filtrate was dried over $Na_2SO_4$, filtered and solvent removed from the filtrate in vacuo, to give a brown greasy solid. The solid was chromatographed (silica gel packed in $CH_2Cl_2$, eluting with $CH_2Cl_2$), fractions containing product were combined and solvent removed in vacuo, giving a pale tan solid. The solid was recrystallised from EtOH, the crystals filtered, washed with hexane and sucked dry, giving 12 as pale yellow crystals (5.09 g, 45%). $^1H$ NMR (299.9 MHz, $CDCl_3$) δ 8.11 (d, J=7.8 Hz, 1H Ar—H), 7.64–7.60 (m, 2H, Ar—H), 7.50–7.42 (m, 3H, Ar—H), 6.88 (d, J=9 Hz, 2H, Ar—H), 1.00 (s, 9H, t-butyl methyl), 0.22 (s, 6H, methyl); $^{13}C$ NMR (125.7 MHz) δ 166.12 (carbonyl), 154.91 (aromatic), 138.09 (aromatic), 132.72 (protonated aromatic), 132.54 (aromatic) 129.72 (protonated aromatic), 127.78 (aromatic), 127.45 (protonated aromatic), 126.82 (protonated aromatic), 124.05 (protonated aromatic), 120.96 (protonated aromatic), 25.71 (t-butyl methyl), 18.27 (tertiary), −4.34 (methyl); Anal Calcd. for $C_{19}H_{23}NO_2SiSe$: C: 56.43, H: 5.73, N: 3.46, found: C: 56.72, H: 5.84, N: 3.56; m.p. 188° C.

2-(4-Hydroxyphenyl)-1,2-benzisoselenazol-3(2H)-one (Compound 13)

To a 0° C. solution of 12 (2.0 g, 4.95 mmol) in THF (25 mL) was added TBAF solution (IM in THF, 14 mL, 14 mmol) dropwise over 15 minutes under a nitrogen atmosphere. The mixture was stirred at 0° C. for 1 hour after which time TLC analysis (silica gel, 19:1 $CH_2Cl_2$/diethyl ether) showed no starting material to be present. The solvent was removed in vacuo to give a brown oil. The oil was dissolved in $CH_2Cl_2$ (50 mL) and the organic phase washed with 5% HCl (150 mL), and $H_2O$ (4×50 mL). Upon the second water wash a yellow solid formed inside the separating funnel. The solid was collected by filtering both phases and residual solid was washed from the funnel in the final two washes. The filtered solid was washed with the final two aqueous extracts, sucked dry and recrystallised from 1:1 EtOH/THF (35 mL). The crystals were collected by filtration, washed with diethyl ether and sucked dry, giving 13 as yellow crystals (1.01 g, 97%). $^1$H NMR (299.9 MHz, d$_6$-DMSO) δ 9.65 (s, 1H, —OH), 8.10 (d, J=7.8 Hz, 1H, Ar—H), 7.91 (d, J=8.4 Hz, Ar—H), 7.70 (dd, 1H, Ar—H), 7.49 (dd, 1H, Ar—H), 7.39 (d, J=9 Hz, 2H, Ar—H), 6.86 (d, J=9 Hz, 2H, Ar—H); $^{13}$C NMR (125.7 MHz, d$_6$-DMSO) δ 165.82 (carbonyl), 156.71 (aromatic), 139.94 (aromatic), 132.87 (aromatic), 131.54 (aromatic), 129.26 (aromatic), 128.75 (aromatic), 127.70 (protonated aromatic), 127.07 (aromatic), 126.71 (aromatic), 116.51 (protonated aromatic); Anal Calcd. for $C_{13}H_9NO_2Se$: C: 53.81, H: 3.13, N: 4.83, found: C:54.04, H: 3.03, N: 4.88; m.p. >260° C.

2-[4-(4-iodobutoxy)phenyl]-1,2-benzisoselenazol-3(2H)-one (Compound 14)

To a suspension of NaH (60% emulsion washed with pentane and dried in vacuo, 60 mg, 1.50 mmol) in dry DMF (1 mL) at 0° C. under argon was added a solution of 13 (300 mg, 1.03 mmol) in dry DMF (7 mL) under argon via a cannula. The resultant solution was stirred for 2 hours at room temperature then added via a cannula to a solution of 1,4-diiodobutane (3.20 g, 10.3 mmol) in dry DMF (2 mL) under argon. The resultant solution was stirred in the dark for 2 days at room temperature under argon. Water (1 mL) was carefully added and solvent removed in vacuo to give an oily residue. The residue was dissolved in $CH_2Cl_2$ (20 mL) and the organic phase washed with $H_2O$ (20 mL), 10% $Na_2S_2O_3$ (20 mL), and $H_2O$ (20 mL). The organic extract was dried over $Na_2SO_4$ and filtered. Solvent was removed from the filtrate in vacuo, giving a yellow oily residue. The residue was chromatographed (silica gel packed in $CH_2Cl_2$, eluting with 19:1 $CH_2Cl_2$/diethyl ether) and fractions containing product were combined. Solvent was removed in vacuo, giving sufficiently pure 14 as a white solid (254 mg, 52%). $^1$H NMR (299.9 MHz, CDCl$_3$) δ 8.11 (d, J=7.8 Hz, 2H, Ar—H), 7.68–7.62 (m, 2H, Ar—H), 7.52–7.43 (m, 3H, Ar—H), 6.94 (d, J=9 Hz, 2H, Ar—H), 4.02 (t, J=5.9 Hz, 2H, —O—CH$_2$—), 3.27 (t, J=6.6 Hz, 2H, —CH$_2$—I), 1.98 (m, 4H, —CH$_2$—CH$_2$—); $^{13}$CNMR (125.7 MHz, CDCl$_3$) δ 166.20 (carbonyl), 158.0 (aromatic), 138.12 (aromatic), 132.73 (aromatic), 132.03 (aromatic), 129.73 (aromatic), 127.73 (protonated aromatic), 127.60 (aromatic), 126.85 (aromatic), 126.85 (aromatic), 124.08 (aromatic), 115.41 (protonated aromatic), 67.32 (—O—CH$_2$—), 30.43 (methylene), 6.64 (—CH$_2$—I); LRAPCI MS (+formic acid) Calcd. For $C_{17}H_{17}NOSeI$: 473, found: 473.

2-[4-(4-triphenylphosphoniobutoxy)phenyl]-1,2-benzisoselenazol)-3(2H)-one iodide (Compound 15)

A dry Kimax tube containing 14 (50 mg, 0.106 mmol) and triphenylphosphine (278 mg, 1.06 mmol) was purged with argon, sealed and placed in the dark. The mixture was stirred as a melt at 90° C. for 2 hours. The mixture was cooled and the solid residue dissolved in $CH_2Cl_2$ (1 mL). Product was triturated with diethyl ether and collected by centrifugation (3500 rpm for 10 minutes). The solid residue was triturated twice more from $CH_2Cl_2$ with diethyl ether and collected by centrifugation. Residual solvent was removed from the precipitate in vacuo, giving crude 15 as a yellow solid (68 mg, 87%). $^1$H NMR (299.9 MHz, CD$_2$Cl$_2$) δ 8.44 (d, J=8.1 Hz, 1H, Ar—H), 7.90 (d, J=8 Hz, 1H, Ar—H), 7.86–7.34 (m, 19H, Ar—H, —P$^+$Ph$_3$), 6.79 (d, J=9 Hz, 2H, Ar—H), 3.97 (t, J=5.7 Hz, 2H, —O—CH$_2$—), 3.41 (m, 2H, —CH$_2$—P$^+$Ph$_3$), 2.04 (m, 2H, —O—CH$_2$—CH$_2$—), 1.87 (m, 2H, —CH$_2$—CH$_2$—P$^+$Ph$_3$); $^{31}$P NMR (121.4 MHz, CD$_2$Cl$_2$) δ 24.29; LRES$^+$ Calcd for $[C_{35}H_{31}NO_2PSe]^+$: 608, found: 608

Accumulation of Compound 9 in Mitochondria

To demonstrate that the targeting of the SOD mimetic to mitochondria is effective and that these compounds can cross the lipid bilayer of the mitochondrial inner membrane, compound 9 was tested in relation to isolated mitochondria.

Liver mitochondria were prepared from female Wistar rats by homogenisation followed by differential centrifugation in medium containing 250 mM sucrose, 10 mM Tris-HCL (pH 7.4) and 1 mM EGTA (Chappell, J. B. and Hansford, R. G., In: Subcellular components: preparation and fractionation (Ed. Birnie G D), pp. 77–91. Butterworths, London, 1972, which is incorporated herein by reference.)

An ion selective electrode for compound 9 was prepared by standard procedures (Kamo, N., et al., *Journal of Membrane Biology*, 49, 105–121 (1979) and Davey, G. P., et al., *Biochemical Journal*, 288, 439–443 (1992), which are incorporated herein by reference), and activated by soaking in 100 μM compound 9 for 1–3 days. The electrodes were then inserted into an air-tight chamber of an oxygen electrode enabling simultaneous measurement of oxygen consumption and compound 9, as shown in FIG. 1.

The rat liver mitochondria (2 mg protein/ml) were suspended in KCl medium (120 mM KCl, 10 mM HEPES, pH 7.2, 1 mM EGTA) with additions of rotenone (5 μg/ml) and nigericin (0.6 nM) in a stirred 3 ml system at 30° C. Compound 9 was titrated in in 1 μM increments (from 650 to 730s on FIG. 1) and the response of the electrode measured over 0–5 μM of Compound 9. This response was logarithmic with respect to the concentration of Compound 9.

Figure 1:
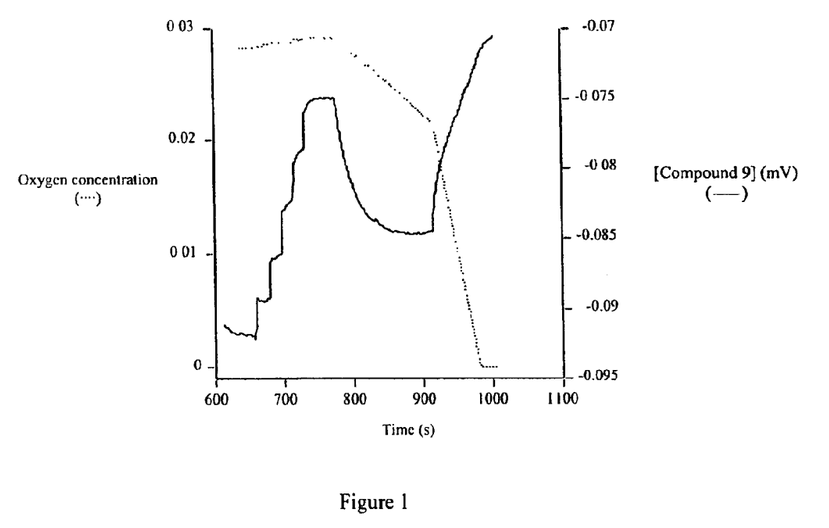
FIG. 1 shows the variation in concentration of Compound 9 and oxygen over time in an experiment to show the take up of compound 9 into the mitochondrial matrix.

To energise the mitochondria, the respiratory substrate succinate (5 mM) was added (at 800s on FIG. 1). These conditions are known to generate a mitochondrial membrane potential of about 180 mV (Burns, et al., *Arch Biochem Biophys*, 332,60–68 (1995); Burns and Murphy, *Arch Biochem Biophys*, 339, 33–39 (1997), which are incorporated herein by reference). As can be seen from FIG. 1, the concentration of compound 9 outside the mitochondria falls rapidly.

When the uncoupler FCCP (carbonyl cyanide-p-trifluoromethoxyphenylhydrazone), which prevents mitochondria establishing a membrane potential (Burns et al., 1995))(332 nM) was added to dissipate the membrane potential (at 900s) the accumulation of compound 9 into mitochondria was reversed, as seen in FIG. 1.

This shows that compound 9 is rapidly and selectively accumulated into mitochondria driven by the mitochondrial membrane potential. This accumulation results in a concentration of the compound within mitochondria of about 1.25 nmol/mg protein, corresponding to ~500-fold accumulation of compound 9 by energised mitochondria. As this accumulation is rapidly (<10 s) reversed by addition of the uncoupler FCCP to dissipate the mitochondrial membrane potential after accumulation of compound 9 within the mitochondria, the mitochondrial specific accumulation of compound 9 is solely due to the mitochondrial membrane potential and is not due to specific binding or covalent interaction.

Antioxidant Efficacy of Compound 9

To see if Compound 9 is catalytically active as a superoxide dismutase mimetic, a standard assay for superoxide dismutase activity was used (Boveris, A., *Methods Enzymol.*, 105, 429–435 (1984), which is incorporated herein by reference).

Figure 2:
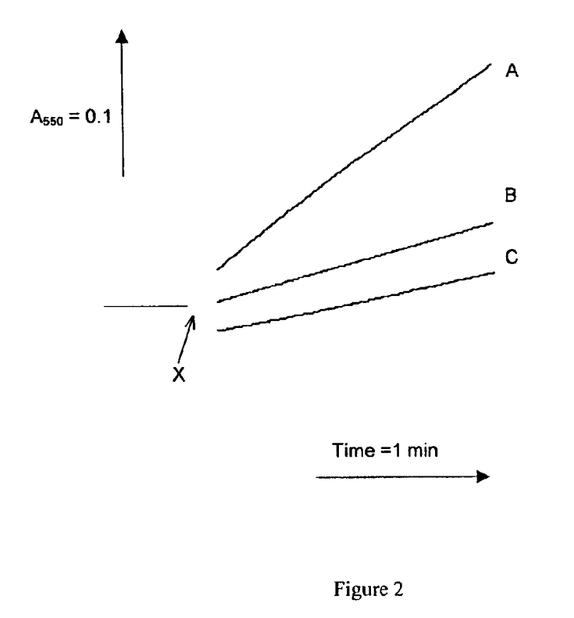
FIG. 2 shows the effect on the absorbance at 550 nM caused by adding Compound 9 (B) or a native SOD enzyme (CuZnSOD) (C) to a system comprising cytochrome c(III) and constant flux of superoxide, against the control line (A)

The incubation conditions were 50 mM KPi, pH 7.5; 1 mM EGTA; 100 μM DTPA (N,N-bis(2-bis[carboxymethyl]amino)ethyl) glycine) at 30° C. to which was added 0.1 unit/ml xanthine oxidase and acetylated cytochrome c (50 μM). After incubation for 2 min, the background rate was measured for 1 min then hypoxanthine (100 μM) was added to initiate superoxide formation (point X in FIG. 2), which provides a continual flux. The rate of superoxide formation is measured by the rate at which the superoxide reduced cytochrome c(III) to cytochrome c(II), which leads to an increase in light absorption at 550 nm ($A_{550}$). SOD activity causes the superoxide to be converted to hydrogen peroxide thereby decreasing the rate of reduction of cytochrome c (III). In FIG. 2, the initial rate of reduction of cytochrome c (III) can be seen (line A) and on addition of compound 9 (250 nM) this rate of cytochrome c reduction was decreased due to consumption of the superoxide by compound 9 (line B). On addition of a native superoxide dismutase enzyme (CuZn-SOD)(0.416 U/ml) the rate of cytochrome c reduction was also decreased (line C).

Control experiments show that compound 9 does not inhibit the activity of xanthine oxidase, and so the activity shown is SOD mimetic activity.

Figure 3:
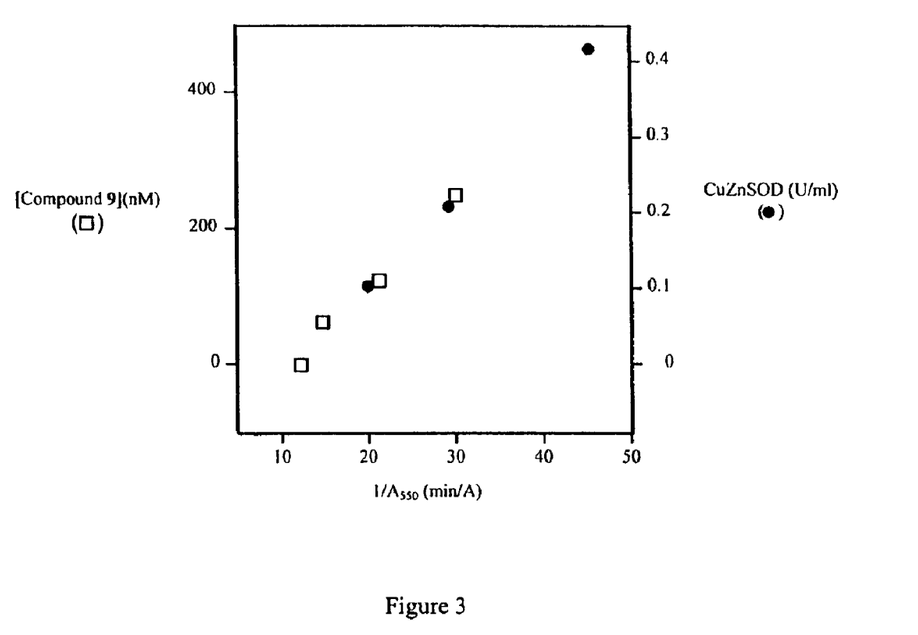
FIG. 3 shows a comparison between the activity of Compound 9 and the native SOD enzyme (CuZnSOD) at various concentrations in the assay used to generate the results shown in FIG. 2.

The above experiments were repeated using various concentrations of Compound 9 and the native superoxide dismutase (Cu, Zn SOD) in order to compare their activity. The results are illustrated in FIG. 3, which shows that the activity of 1 nmol Compound 9 corresponds to about 1 unit activity of the native enzyme CuZnSOD, and consequently Compound 9 is an effective SOD mimetic and will protect mitochondria from oxidative damage.

What is claimed is:

1. A compound comprising a lipophilic cation moiety covalently coupled to an antioxidant moiety which is a superoxide dismutase (SOD) mimetic wherein the lipophilic cation moiety is a tribenzyl or triphenyl substituted ammonium or phosphonium moiety.

2. A compound as claimed in claim 1 having the formula where L is a linking group and Z is an anion.

3. A compound as claimed in claim 1, wherein the SOD mimetic moiety comprises at least one manganese atom in either oxidation state II or III.

4. A compound as claimed in claim 3, wherein the SOD mimetic moiety is selected from the group consisting of: Mn III metalloporphyrins, Mn II-salen complexes and Mn-II pentaazamacrocyclic ligand-based compounds.

5. A compound as claimed in claim 4, wherein the SOD mimetic moiety is:

6. A compound as claimed in claim 1, wherein the lipophilic cation moiety is triphenyl phosphonium.

7. A compound as claimed in claim 2, wherein the linking group is an alkylene group having 1 to 30 carbon atoms, optionally comprising O, S or NH at the SOD mimetic moiety end.

8. A compound as claimed in claim 2, wherein Z is a pharmaceutically acceptable anion.

9. A compound as claimed in claim 2, wherein the compound is of formula:

10. A compound as claimed in claim 9, wherein the compound is of the formula:

wherein X is selected from the group consisting of O and S, and n is from 1 to 30.

11. A pharmaceutical composition comprising a therapeutically effective amount of a compound as defined in claim 1 in combination with one or more pharmaceutically acceptable carriers or diluents.

* * * * *